US005334123A

United States Patent [19]

Rutherford

[11] Patent Number: 5,334,123

[45] Date of Patent: Aug. 2, 1994

[54] TILTING EXERCISE APPARATUS FOR THE BACK

[76] Inventor: Wayne Rutherford, P.O. Box 546, Yucca Valley, Calif. 92286

[21] Appl. No.: 910,425

[22] Filed: Jul. 8, 1992

[51] Int. Cl.[5] .......................... A63B 21/00; A61F 5/00

[52] U.S. Cl. .................................... 482/144; 482/133; 482/111; 601/24

[58] Field of Search ................. 482/92, 133, 144, 142, 482/122, 123, 112, 31; 297/300, 304; 128/24 R

[56] References Cited

U.S. PATENT DOCUMENTS

| | | | |
|---|---|---|---|
| 3,081,085 | 3/1963 | Girolamo | 482/144 |
| 3,286,708 | 1/1966 | Gartner | 482/144 |
| 3,794,023 | 2/1974 | Bradley | 128/24 R |
| 4,214,790 | 7/1980 | Sieber | 482/144 |
| 4,419,989 | 12/1983 | Herbold | 482/142 |
| 4,645,197 | 2/1987 | McFee | 482/31 |
| 5,110,121 | 5/1992 | Foster | 482/142 |
| 5,110,122 | 5/1992 | Moore et al. | 482/123 |
| 5,125,884 | 6/1992 | Weber et al. | 482/142 |

*Primary Examiner*—Richard J. Apley
*Assistant Examiner*—Jerome Donnelly
*Attorney, Agent, or Firm*—Andrew Jordan

[57] ABSTRACT

A rearwardly tiltable chair set sturdily in a frame. The chair allows a user thereof to tilt back and thereby decompress the spine. The user may subsequently engage in exercises that flex, stretch, and strengthen the spine and its accompanying tendons, ligaments and muscles. The user is tilted back to a limited degree so that while the spine is allowed to decompress, blood does not rush to the head. The chair is pivotably held by the frame and tilts easily backward or forward so that the user can easily control his position. In an alternative embodiment, a resistive element is interposed between the back of the chair and the floor so that the user can exercise by pressing back upon the resistive element with the upper torso. A gauge may be coupled to the resistive element to measure the force applied by the user to the resistive element.

1 Claim, 5 Drawing Sheets

TILTING EXERCISE APPARATUS FOR THE BACK

BACKGROUND OF THE INVENTION

1. Field of the Invention

This invention relates to back exercise machinery, and more particularly to a device that tilts the user backwards so that the spine may be exercised and stretched while it is not compressed.

2. Description of the Related Art including information disclosed under 37 C.F.R. SS 1.97–1.99.

The human spine allows people to walk in an upright manner and is adapted to undergo many stresses. However, with these stresses, the spine is also subject to a number of injuries, disabilities, and diseases that cause many people severe discomfort and pain.

The act of walking upright exerts a significant amount of stress upon the spine as the spine supports the entire upper torso. Through years of use, the accumulation of injuries, and the onset of increasing age, the spine can become less limber and more prone to injury and disease. Pinched nerves and diseased discs are two of but several painful conditions that originate from the spine.

One reason the spine becomes a focal point of injury and disease is that for most of the waking hours, the spine is continually subject to compressive and downward forces. As the base of the spine is held fixed by the pelvic girdle, the upper portion of the body pushes downward upon the spine to compress the several vertebrate together. As this downward, compressive force upon the spine is continually exerted upon it day after day, small injuries and/or insults can be inflicted upon the spine. Further, such small injuries or insults can be exacerbated by the ongoing daily stresses upon the spine. As only a healthy spine can move and articulate properly, any injury or insult to the spine can inhibit normal movement and can even make bedridden an otherwise healthy person.

One way to avoid injury to the spine is to strengthen it by exercise. Exercise works to strengthen other parts of the body, and to help them to withstand injuries. The same is true of the spine. With proper exercise, the spine can become a stronger member of a healthy body and can improve a person's posture and overall well-being. While exercise improves the spine, typical exercises only work the spine in its usual, compressed state. The spine would be made stronger and more healthy by exercising it while it was in a decompressed state and would greatly complement spinal exercises that work on the spine while in its normal compressed state.

In order to better exercise the spine when it is decompressed, devices have been developed that turn a person upside-down so that the spine can be stretched and flexed while the spine is not subject to its downward compressive forces.

One such device is in the form of a pair of boots that attach to the person's feet in a snug and secure manner. Attached to the boots are a pair of large hooks that serve to support the person by engaging a sturdy bar. The bar is fixed in position at a height somewhat above the height of the person. The person grabs the bar, swings the boots up to the bar, and engages the boot hooks on the bar. The person then releases the bar with his hands, but stays attached to the bar with his feet. Gravity then exerts a downward pull on the now free-swinging body of the user so that previously compressed skeletal structures are allowed to stretch out.

In this position, the user can flex and stretch the spine with its accompanying ligaments and tendons. As the upper portion of the body now pulls downward on the spine, the compressive forces previously exerted upon the spine are removed, allowing the intervertebral discs some room to maneuver and to re-seat themselves between the vertebrae. Other spinal structures may also re-align themselves. When the person is through exercising, the person grasps the bar and disengages the boot hooks from the bar to lower the feet to the ground.

Several problems arise from the use of such "gravity boots". Once the user has disengaged the bar with his hands and swings free, blood from the lower extremities flows towards the head as the head is now the lowest part of the body. The upside-down position attained by the body also changes the pressure exerted by the blood on the body, including the head. It is possible for the shift in blood flow to exert such pressures upon the head and brain that blood vessels inside the head may burst, possibly causing a stroke.

It may also be difficult for someone using gravity boots to disengage the boots from the bar. Having attained an upside-down position, the user must reach back up to the bar by raising the hands and torso up to the bar. If due to physical weakness or immobility the user cannot reach the bar, he or she will not be able to disengage the boots from the bar. Unless the user is aided by another, he or she will be left hanging indefinitely.

Another device that has been developed to relieve spinal pressure for exercise uses a rotating bar or wheel that allows the user to engage the apparatus from an upright position and then to turn himself upside-down by rotating around a central hub located at a height approximately at the user's midsection.

Such a device allows the user to disengage himself by rotating the device from an upside-down position to a right side-up position, avoiding the problem of indefinite hanging present with the gravity boot device. However, the problems associated with blood flow and pressure upon the brain remain and can have the same catastrophic consequences as with the gravity boots.

For both of these devices, the user decompresses the spine by hanging upside-down. However, hanging upside-down does not decompress the entire spine as the curve of the lower back is maintained. When a person hangs upside-down, the curve of the lower spine is only removed when the person pulls his knees slightly toward his chest, an act that is only achieved with great difficulty while freely hanging upside-down. As the curve of the spine at the lower back is maintained by gravity boots and the rotating apparatus, a person cannot entirely decompress the spine. Any stretching or exercise performed by the user by necessity does not stretch or exercise an entirely decompressed spine.

While for those of more robust constitutions, the act of turning oneself upside-down presents no problems, and may even be a pleasant change in an exercise regimen, those of weaker constitutions or more frail dispositions may require exercise or the ability to stretch in a position that relieves the downward and compressive stress normally imposed upon the spine. Using the devices mentioned above, people with more delicate health conditions are subject to some, even catastrophic, risk.

It can be seen that those who would exercise their spine in a stretched condition have a need for a device that allows decompression of the spine without exerting undue pressure upon the user. A further need is also present in that such a device should be easily engaged and disengaged by the user. Such a device should also remove at least somewhat the curvature present in the spine so that the entire spine can be stretched and flexed.

SUMMARY OF THE INVENTION

The present invention resides in a tiltable chair apparatus that pivots backward upon a sturdy frame. The tiltable chair allows the user to decompress his spine, while temporarily removing some of the spine's curvature. Although the user's spine is decompressed, the tiltable chair does not turn the user entirely upside-down and avoids the problems associated with altered blood flow and pressure to the brain.

The user sits in the seat and straps himself securely in position to the tiltable chair. A small padded portion of the seat lifts the user's knees slightly in order to allow better relaxation of the spine. Once in position, the user easily and conveniently pivots the chair about the frame until the top of the chair reaches the floor. The user is then tilted backwards at about a thirty degree (30°) angle. The user's spine is thereby decompressed, and the user may flex and exercise it in a relatively upside-down position without applying the full force of the bloodstream upon the brain. Further, the user can easily tilt himself upright without great effort.

In an alternative embodiment, a resistive or restoring element (such as a hydraulic piston system or a spring) can be used in conjunction with the exercise apparatus so that once the user is tilted back, the user can exercise by leaning backwards into the back support of the chair member against the resistive element. In this way, muscles supporting the back and certain abdominal muscles are exercised.

OBJECTS OF THE INVENTION

It is an object of the present invention to provide means by which a person's spine may be decompressed for exercise and stretching.

It is an object of this invention to provide spinal decompression means that are safer than some present spinal decompression means.

It is an object of this invention to decompress the spine without subjecting the brain to greatly altered blood flow and pressure.

It is an object of this invention to provide spinal decompression means that are easily engaged and likewise, easily disengaged.

It is an object of this invention to provide spinal decompression means that decompress the entire spine, including the vertebrae of the lower back.

It is an object of this invention to promote good health by enabling a user to stretch and exercise the spine while the spine is not compressed.

It is an object of this invention to provide means by which the muscles of the back and abdomen may be exercised while the spine is decompressed.

These and other objects and advantages of the present invention will be apparent from a review of the following specification and accompanying drawings.

DESCRIPTION OF THE PREFERRED EMBODIMENT(S)

Figure 1:
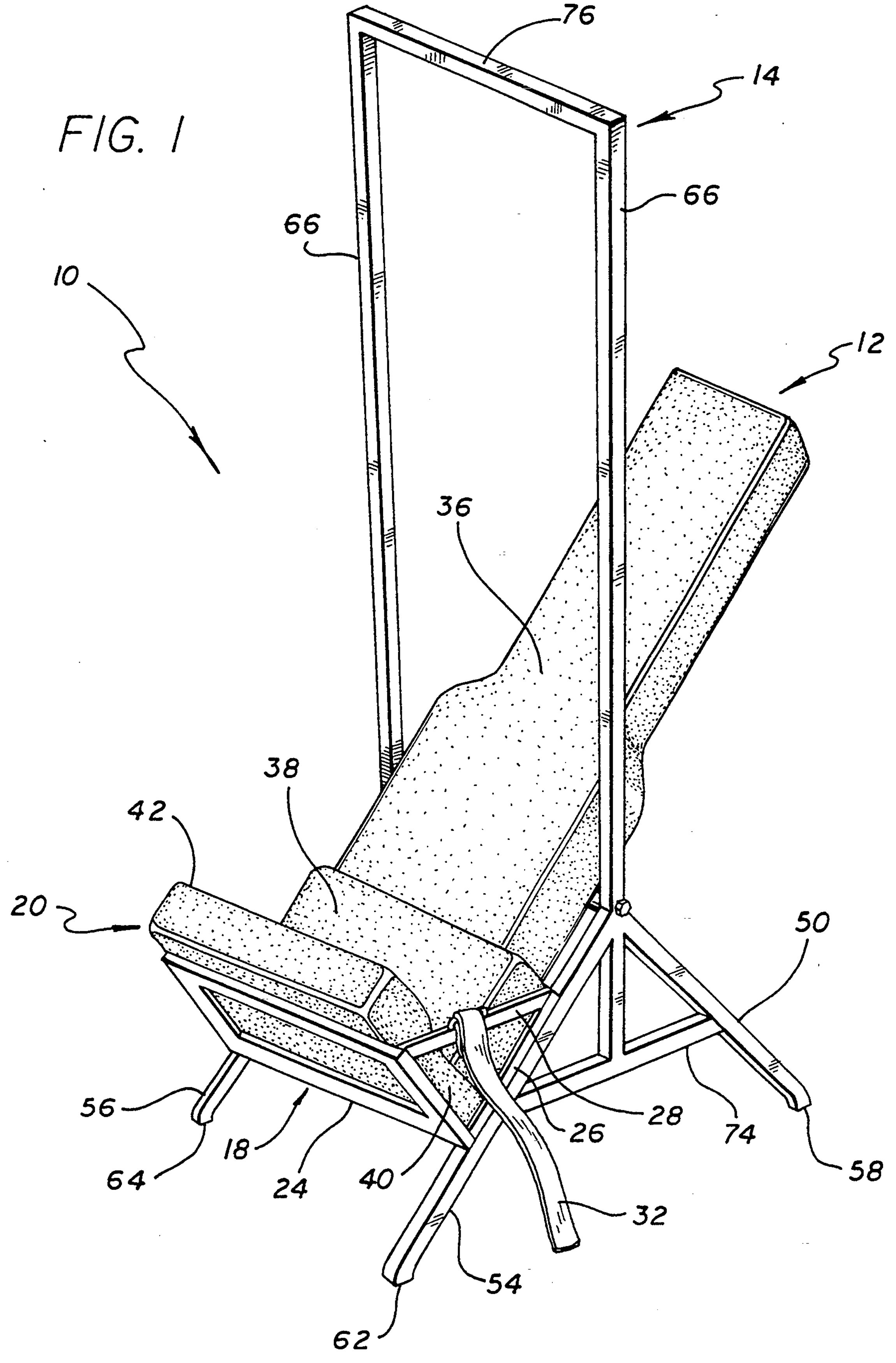
FIG. 1 is a front perspective view of the tilting exercise apparatus for the back.
Figure 2:
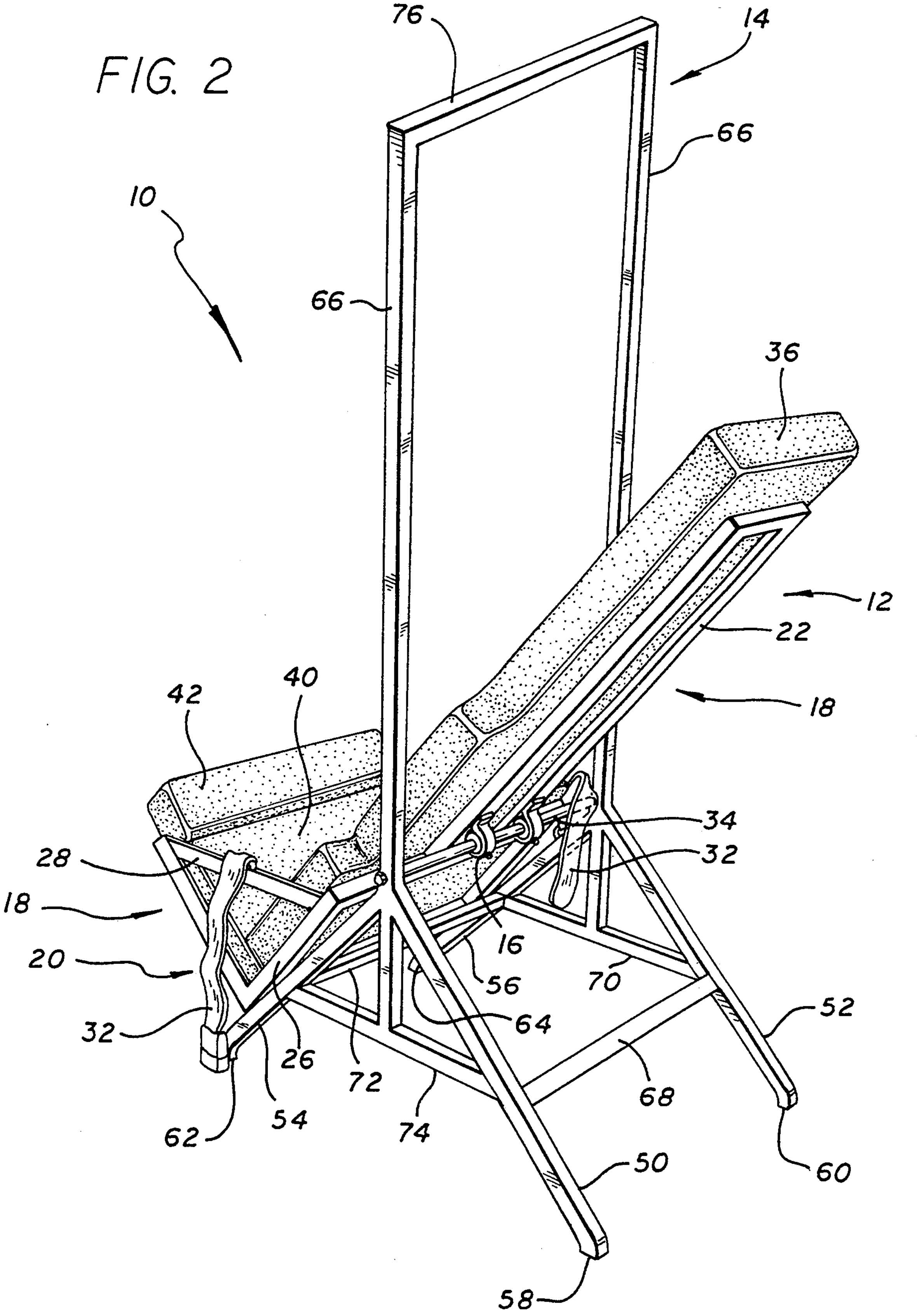
FIG. 2 is a rear perspective view of the tilting exerciser.
Figure 3:
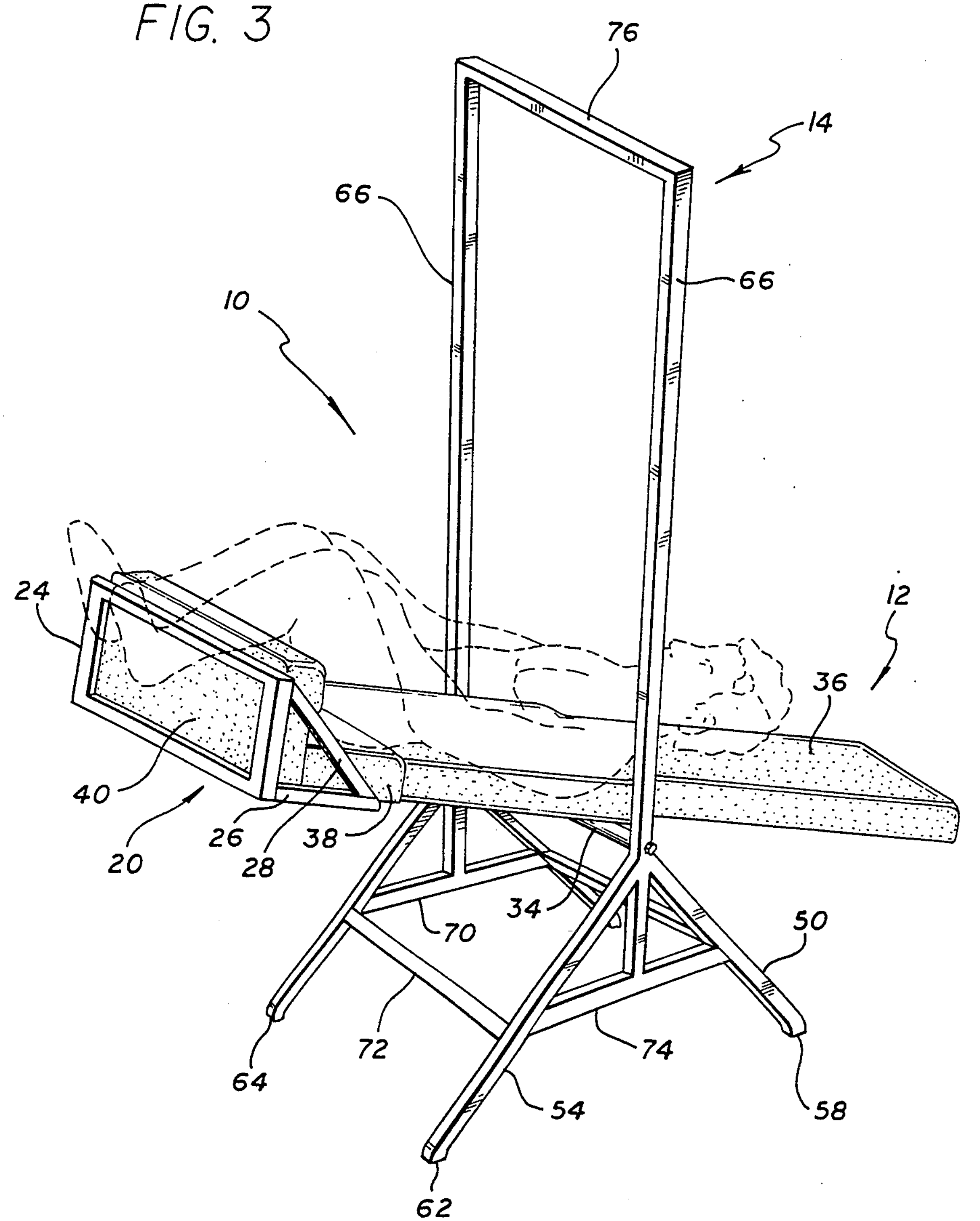
FIG. 3 is a front perspective view of the tilting exerciser with the chair portion tilted back and showing a person using the device in phantom.
Figure 4:
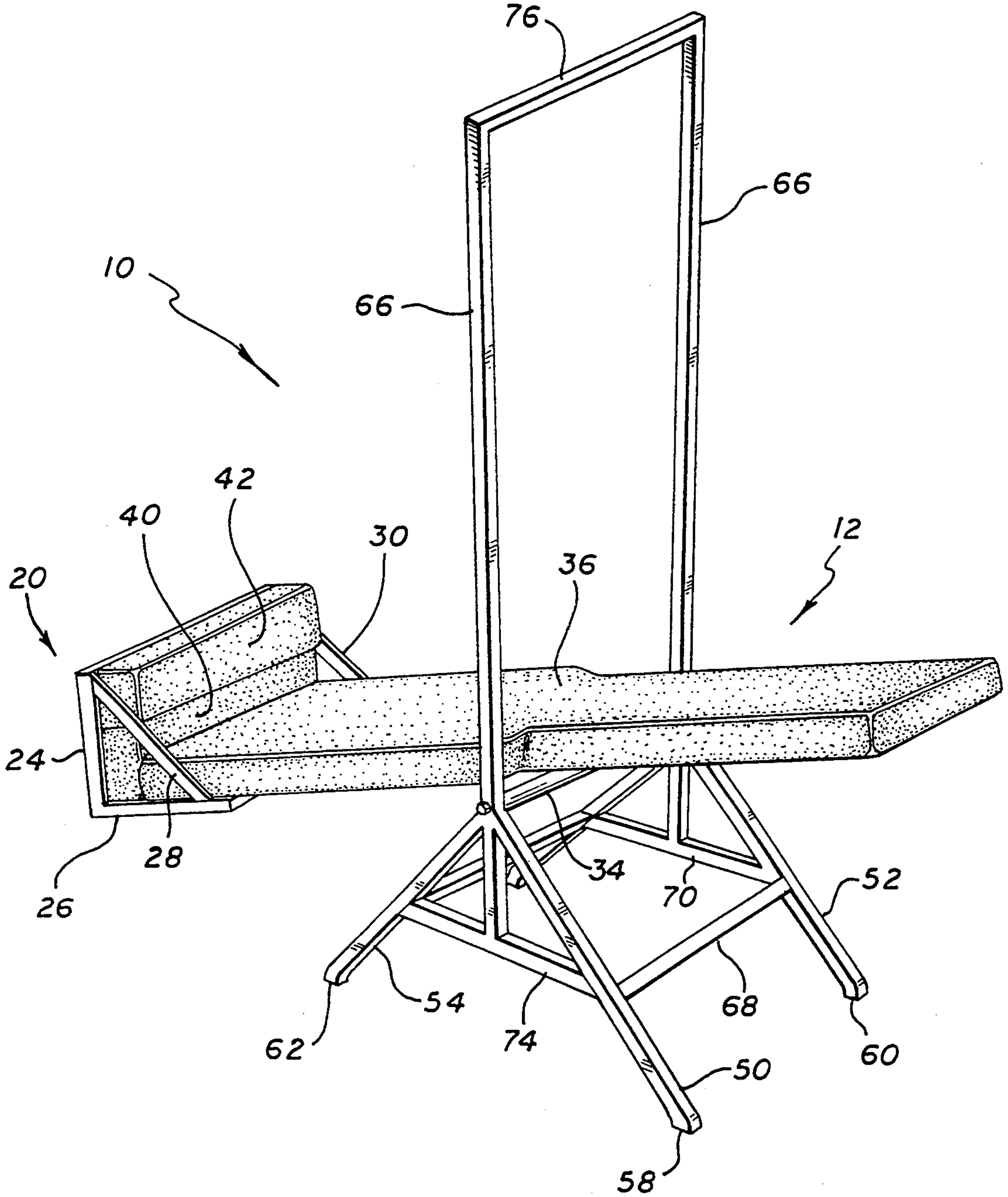
FIG. 4 is a rear perspective view of the tilting exerciser with the chair portion tilted back.

Referring to FIGS. 1 and 2, the tiltable exerciser for the back of the present invention is generally referred to by reference numeral 10. A chair or seat 12 is pivotably attached to a sturdy frame 14. The frame 14 securely supports the chair 12 when the chair is in both its upright forward position (FIGS. 1 and 2) or in its tilted back position (FIGS. 3 and 4). A pillow block bearing 16 serves to allow the chair 12 to pivot about the frame 14.

The chair 12 has a chair frame 18 that supports padded cushions to provide greater comfort for the user. The chair frame 18 has a lower hip-supporting section 20 and an upper back-supporting section 22. The lower hip-supporting section 20 has a bottom or lower supporting section 24 and a rear supporting section 26. The lower supporting section 24 is connected at a right angle to the rear supporting section 26 so that support is provided for the pelvis of the user.

Angle bars 28 and 30 provide additional support for the lower hip-supporting section 20 by connecting the otherwise free ends of the lower supporting section 24 and the rear supporting section 26.

A belt or straps 32 can be attached to the angle bars 28, 30. The belt 32 can be similar in construction to those used in automobiles that have a metal end fitting into a releasable buckle. However, any belt or strap arrangement that securely holds the user in position while using the exercise device 10 may also be used. Also, so long as the structural integrity of the lower hip-supporting section 20 is maintained, angle bars 28, 30 are not required or may be substituted by other supporting structures. If angle bars 28, 30 are not used, the belt or strap 32 can be otherwise attached to the lower hip-supporting section 20 of the chair frame 18.

The upper back-supporting section 22 of the chair frame 18 is connected to and extends further from the rear supporting section 26 of the lower hip-supporting section 20.

The pillow block bearing 16 is connected to the upper back-supporting section 22 just above the lower hip-supporting section 20. The pillow block bearing 16 remains fixed with respect to the upper back-supporting section 22, but rotates around the middle crossbar 34.

Flat pieces of material, such as plywood or otherwise, can be fitted against the chair frame 18 to provide underlying support for cushions 36, 38, 40. The cushions 36, 38, 40 serve to provide a comfortable seat for the user. A back cushion 36 comfortably supports the user's back and head. A rear pelvic cushion 38 serves to comfortably support the rear of the user's hips. A seat cushion 40 provides lower support for the user.

Of special note with the seat cushion 40 is the padded bar 42 that fits beneath the user's legs. The padded bar 42 serves to lift the user's thighs and knees and to urge them slightly towards the user's chest. In so urging the user's knees towards his chest, the user's hips are necessarily forced to rotate slightly forward. By rotating forward, the user's hips remove the curve in the lower part of the spine and allow that part of the spine to be decompressed when the user tilts backwards. The rotation of the user's hips is maintained when the user tilts back in the chair 12.

The frame 14 provides the secure support required by the chair 12 when the chair 12 tilts back. Four legs 50, 52, 54, 56 provide ultimate support for the tilting exerciser 10. Small feet 58, 60, 62, 64 connected to the legs engage the floor or other surface and provide flat surfaces by which the legs can engage the floor.

The legs 50, 52, 54, 56 extend upwardly at an angle, with the legs at the rear of the exerciser extending towards the corresponding legs at the front of the exerciser. The front 54, 56 and rear 50, 52 legs meet just below the connection of the middle crossbar 34 with the upper portion 66 of the frame 14. Lower crossbars 68, 70, 72, 74 connect the individual legs of the frame 14, each leg connected by a crossbar to the two adjacent legs. Interconnected by the lower crossbars 68, 70, 72, 74, the legs 50, 52, 54, 56 provide stability for the exerciser 10, no matter what position the chair 12 attains.

Extending upwardly from the middle of the lower crossbars 70, 74 at the sides of the exerciser 10 is the upper portion 66 of the frame 14. The upper portion 66 intersects the connection of the front and rear legs on either side of the exerciser 10. The middle crossbar 34 connects to the upper portion 66 at both sides just above the junction of the upper portion 66 with the legs. A top crossbar 76 connects the upper ends of the upper frame 66 together. In an alternative embodiment, the top crossbar 76 may be absent with the exposed ends of the upper portion 66 capped or otherwise covered to prevent injury.

As contemplated, the frame 14 and the chair frame 18 are constructed of tubular steel or the like. The exerciser stands approximately 48 inches tall from the floor to the top crossbar 76. Each leg is approximately 20 inches long and makes an angle of approximately forty-five degrees (45°) with the floor. The front 54, 56 and rear 50, 52 legs are approximately 29 inches apart. The middle crossbar 34 is approximately 15½ inches off the floor.

With respect to the chair frame 18, the lower hip-supporting section 20 is approximately 20½ inches wide. The lower supporting section 24 extends out and away from the rear supporting section 26 approximately 11½ inches. The rear supporting section 26 is approximately 11½ inches tall. The upper back-supporting section 22 of the chair frame 18 extends upwardly approximately 33½ inches and is approximately 5 inches wide at its top.

The middle crossbar 34 is connected to the upper back-supporting portion through the pillow block bearing 16 approximately 15½ inches from the bottom of the lower hip-supporting section 20, which is approximately the same as 4 inches above the lower hip-supporting section 20. This point is approximately one-third of the way from the lowest portion of the chair frame 18 to the top of the chair frame 18. This ratio of one-third to two-thirds helps users to tilt the chair backwards and forwards with ease as it places the pivot near the user's center of gravity.

When the chair 12 is tilted back, the top of the chair 12 comes into contact with the floor to stop the chair 12 from further rotating about the middle crossbar 15. When the chair 12 is tilted so that it does touch the floor, the back of the chair 12 forms an angle with the floor of approximately thirty degrees (30°).

In order to use the exerciser 10, a person first sits down in the chair 12 and securely straps himself in with the belt 32. Having secured himself to the chair, the user then places his hands on the upper frame portion 66 by reaching over his head but within the upper frame portion 66. Placing his hands upon the upper frame portion 66, the user presses against the upper frame portion 66 to push himself back into the chair 12 and so to tilt the chair 12 about the middle crossbar 34. The user continues to press upon the upper frame portion 66 until his center of gravity shifts across the middle crossbar 34. At that point, the chair 12 will remain in the rearwardly tilted position until the user pulls himself forwards and towards the upper frame portion 66.

The relative positioning of the chair 12 and its frame 18 with respect to the middle crossbar 34 in such that the user has a minimum amount of difficulty in tilting the chair 12 either forwards or backwards.

While the user is tilted back in the chair 12, the belt 32 serves to secure him in position, ensuring that he does not slide backwards and out of the chair 18. By lifting up the thighs and knees, the padded bar 42 rotates the user's hips forward to help remove curvature otherwise present in the spine. The force of gravity pulls the user down, decompressing the spine and allowing the user to flex, exercise, and stretch while the spine is in a decompressed state.

Weights such as carried in the hand may be used to further urge the vertebra apart. The user need only hold the weights in his in order to further decompress the spine. Exercises may be performed with the hand weights and/or the user can stretch, twist, and flex the spine. Further exercises may be devised by the user, taking advantage of the decompressed nature of the spine while the user is tilted back in the exerciser 10.

Figure 5:
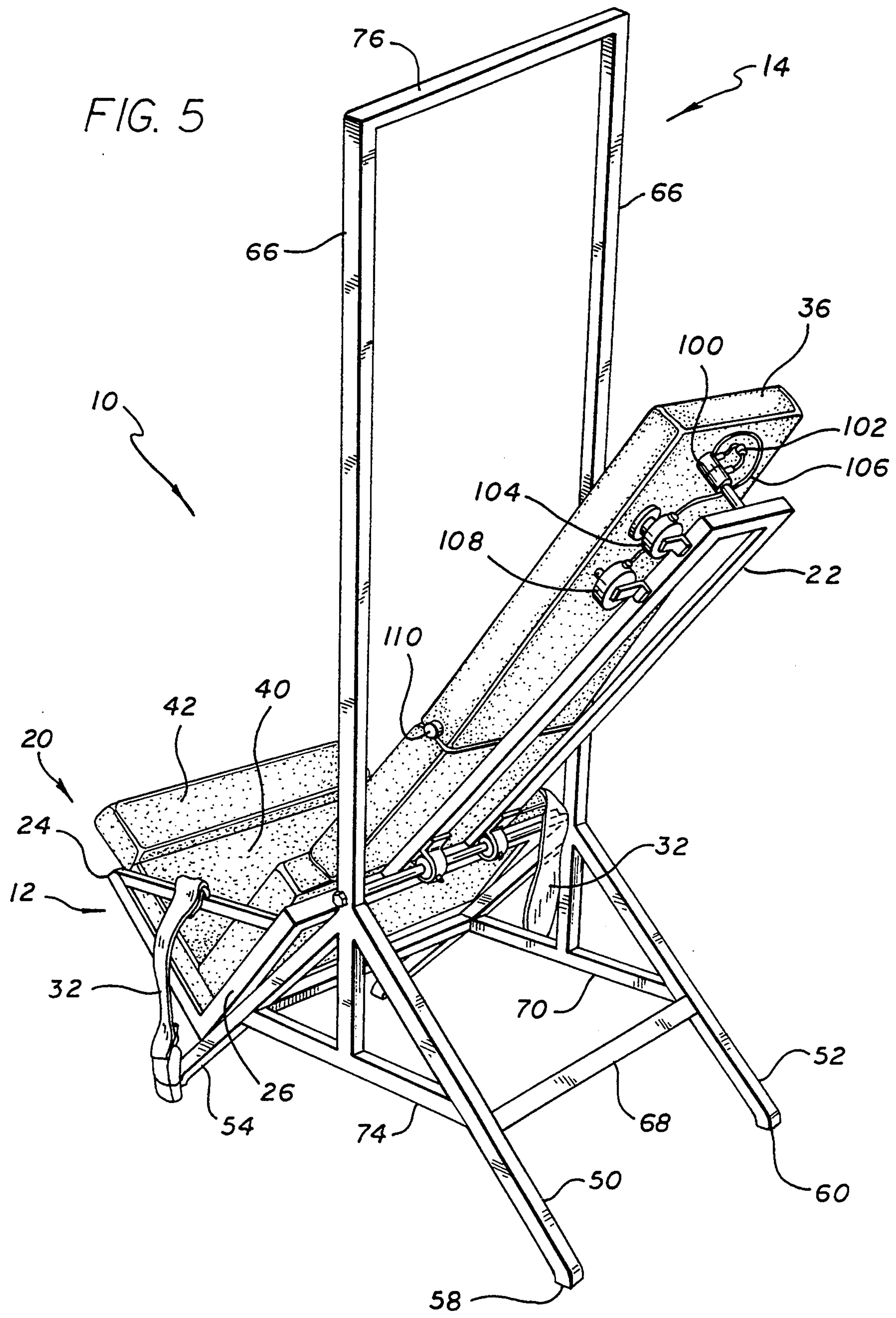
FIG. 5 is a rear perspective view of the tilting exerciser including a resistive element in the form of a hydraulic piston.

As shown in FIG. 5, an alternative embodiment of the present invention resides in providing a resistive element 100 between the upper back-supporting section 22 of the chair frame 18 and the back cushion 36. The resistive element 100 may be similar to a shock absorber used in automobiles, but on a much smaller scale. Fluid within the resistive element 100 can travel through a small valve 102, allowing the resistive element 100 to return to its original condition with the back cushion 36 spaced away from the upper back-supporting section 22 of the chair frame 18.

In order to control the pressure required by the user to push the back cushion 36 against the upper back-supporting section 22 of the chair frame 18, an adjustable valve 104 is coupled to the resistive element 100 via a small hydraulic line 106. As the aperture within the adjustable valve 104 is changed, more or less fluid is allowed to escape from the resistive element during a certain period of time. When less fluid is allowed to escape, more pressure is required to move the back cushion towards the upper back-supporting section 22 of the chair frame 18. When more fluid is allowed to escape, less pressure is required.

In order to detect and measure the pressure applied by the user, a pressure meter is used 108. The pressure meter 108 is connected to the small hydraulic line 106 and is able to register pressure applied on the line 106 regardless of the flow of the hydraulic fluid inside. The pressure meter 108 has a visible read out so that the user can determine what pressure he or she applies. By comparing meter values from different times, the user can determine any progress such as by increased strength.

In order to allow the back cushion 36 to move towards and away from the upper back-supporting section 22 of the chair frame 18, a hinge 110 is provided in the back cushion 36 so that the back cushion has a pivotable connection with the chair 12. While the adjustable valve 104 and the pressure meter 108 are shown in FIG. 5 as being attached to the back of the chair 12, it is also possible that they may be positioned so as to be within easy view and reach of the user. Also, the resistive element 100 may be an adjustable spring.

If for some reason the user needs to extricate himself quickly from either the upright or inverted position, the user can press the release button on the straps 32 buckle and remove himself from the chair 12. In the upright position, the user need only stand up to get away from the exerciser 10. In the inverted position, the user will slide to the floor and away from the chair 12 once the release button has been pushed. The release button serves as a way that the user can quickly and without injury remove himself from the chair 12 should the need arise.

While the present invention has been described with regards to particular embodiments, it is recognized that additional variations of the present invention may be devised without departing from the inventive concept.

What is claimed is:

1. An exercise apparatus for decompressing the spine, comprising:

a frame;

a chair, said chair having a lower hip-supporting section and an upper back-supporting section, said upper back-supporting section connected to said lower hip-supporting section so as to extend upwardly from said lower hip-supporting section;

said lower hip-supporting section having a lower supporting section connected to a rear supporting section, said lower supporting section extending from said rear supporting section;

said chair pivotably coupled to said frame at a point approximately one-third of the length of said chair from a lowest portion of said chair when said chair is upright, said chair comprising a padded bar and a belt, said padded bar connected to a forward portion of said lower supporting section and urging said user's knees slightly towards said user's chest so that said user's hips are rotated slightly forwards to remove at least some curvature from said user's spine while using the exercise apparatus and said belt securing said user to said chair, said chair also comprising:

a back cushion, said back cushion pivotably coupled to said upper back-supporting section; and a resistive element, said resistive element connected between said upper back-supporting section and said back cushion and able to contact and expand so that said upper back-supporting section and said back cushion may move with respect to each other, whereby a user of said exercise apparatus may exert pressure against said resistive element in order to exercise; and a pivotable bearing, said pivotable bearing establishing said pivotable coupling between said frame and said chair; whereby when said chair is fully tilted backwards, said upper back-supporting portion of said chair forms an angle with the floor of approximately thirty degrees (30°) and a user may seat himself in said chair and tilt said chair backwards to decompress said user's spine.

* * * * *